US008258322B2

(12) United States Patent
Mikaylo et al.

(10) Patent No.: US 8,258,322 B2
(45) Date of Patent: Sep. 4, 2012

(54) SYNTHESIS OF HEXAHYDRODIBENZOPYRANONES

(75) Inventors: Valeriy Mikaylo, Toronto (CA); Subakar Paramanantham, Scarborough (CA); Ilya Avrutov, Thornhill (CA); Martyn A. Brown, Toronto (CA); Zemin Li, Toronto (CA); Natalie Lazarowych, Toronto (CA)

(73) Assignee: Watson Laboratories, Inc., Corona, CA (US)

( * ) Notice: Subject to any disclaimer, the term of this patent is extended or adjusted under 35 U.S.C. 154(b) by 386 days.

(21) Appl. No.: 12/549,919

(22) Filed: Aug. 28, 2009

(65) Prior Publication Data

US 2010/0056811 A1  Mar. 4, 2010

Related U.S. Application Data

(60) Provisional application No. 61/092,495, filed on Aug. 28, 2008.

(51) Int. Cl.
*C07D 311/80* (2006.01)
(52) U.S. Cl. ........................................ 549/391
(58) Field of Classification Search .................... 549/391
See application file for complete search history.

(56) References Cited

U.S. PATENT DOCUMENTS

| 4,054,582 | A | 10/1977 | Blanchard et al. | 260/345.3 |
| 4,054,583 | A | 10/1977 | Blanchard et al. | 260/345.3 |
| 4,131,614 | A | 12/1978 | Ryan | 260/345.3 |
| 4,140,701 | A | 2/1979 | Ryan | 260/345.2 |
| 4,148,809 | A | 4/1979 | Day et al. | 260/345.3 |
| 4,171,315 | A | 10/1979 | Ryan | 260/345.3 |
| 4,395,560 | A | 7/1983 | Ryan | 549/391 |
| 4,599,327 | A | 7/1986 | Nogradi et al. | 514/58 |

FOREIGN PATENT DOCUMENTS

| DE | 2729817 C2 | 5/1982 |
| DE | 2729816 C2 | 7/1982 |

OTHER PUBLICATIONS

Altundas et al. "Excellent and Convenient Procedures for Reduction of Benzene and Its Derivatives" Turk J Chem 2005 vol. 29: 513-518.
Archer et al. "Cannabinoids.3. Synthetic Approaches to 9-Ketocannabinoids. Total Synthesis of Nabilone" The Journal of Organic Chemistry 1977 vol. 42(13): 2277-2284.
Birch, A. J. "Reduction by Dissolving Metals. Part VIII. Some Effects of Structure on the Course of Reductive Fission" J. Proc. R. Soc. N.S.W. 1949 vol. 83: 245-250.
International Search Report issued Nov. 24, 2009 of PCT/CA2009/001207.
J. Diederen, Extended European Search Report in EP 09809161, Sep. 14, 2011, European Patent Office, Netherlands.

*Primary Examiner* — Bernard Dentz
(74) *Attorney, Agent, or Firm* — Florek & Endres PLLC

(57) ABSTRACT

An improved process is provided for the synthesis of hexahydrodibenzo[b,d]pyran-9-ones, such as nabilone.

12 Claims, No Drawings

SYNTHESIS OF HEXAHYDRODIBENZOPYRANONES

RELATED APPLICATIONS

This application claims the benefit of U.S. Provisional Application No. 61/092,495, filed Aug. 28, 2008, and Canadian Patent Application No. 2,638,940, filed Sep. 22, 2008, the entire contents of both of which are incorporated herein by reference.

FIELD OF THE INVENTION

The present invention relates to an improved synthesis of hexahydrodibenzo[b,d]pyran-9-ones, such as nabilone.

BACKGROUND OF THE INVENTION

Nabilone is the generic name for 6a,10a-1-hydroxy-3-(1,1-dimethylheptyl)-6,6-dimethyl-6,6a,7,8,10,10a-hexahydro-9H-dibenzo[b,d]pyran-9-one. The pharmaceutically active and marketed form of nabilone (and what is typically understood by the term nabilone) is trans-nabilone, namely 6a,10a-trans1-hydroxy-3-(1,1-dimethylheptyl)-6,6-dimethyl-6,6a,7,8,10,10a-hexahydro-9H-dibenzo[b,d]pyran-9-one:

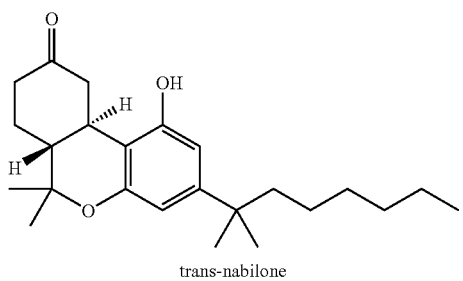

trans-nabilone

Trans-nabilone is typically a racemic mixture consisting of the (6aS,10aS) and the (6aR,10aR) isomers.

Nabilone is a synthetic cannabinoid which mimics the main ingredient of marijuana (THC), though it is not derived from the cannabis plant. It is typically used for the treatment of chemotherapy-induced nausea and vomiting for patients that do not respond to conventional anti-emetics (anti-nausea medications). It has also been used in the treatment of anorexia and weight loss in patients with AIDS, and as an adjunct therapy for chronic pain management. Case studies have also demonstrated various benefits for conditions such as fibromyalgia and multiple sclerosis.

Nabilone is one of a class of compounds known as hexahydrodibenzopyranones. In view of the clinical usefulness of nabilone and related dibenzopyranones, efforts have been made to find improved and alternative methods for the preparation of such compounds. The original synthesis of 6a,10a-trans-hexahydrodibenzopyranones suffered from being multistep and of low overall yields, in addition to providing substantial mixtures of 6a,10a-cis and 6a,10a-trans isomers, the separation of which is difficult; see U.S. Pat. No. 3,507,885.

A three-step synthesis of 6a,10a-cis-hexahydrodibenzopyranones was published by Archer, et al., J. Org. Chem., 42, 2277 (1977). Archer et al. also provided a method for converting the 6a,10a-cis isomers to the corresponding 6a,10a-trans isomers; see U.S. Pat. No. 4,054,582 and Archer et al., J. Org. Chem., 42, 2277 (1977). Archer's synthesis is outlined below:

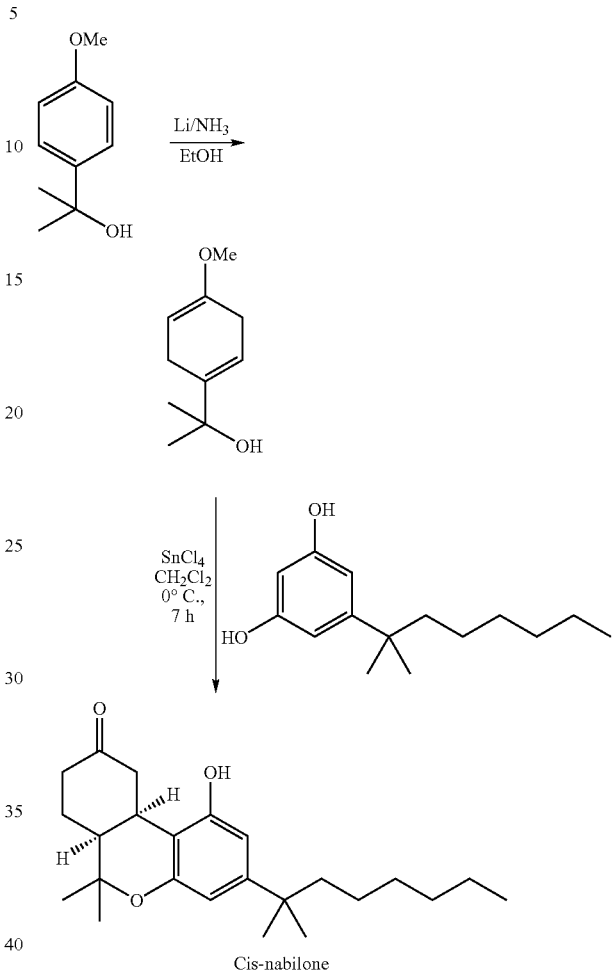

Cis-nabilone

Large scale commercial use of the above synthesis is problematic. Archer et al use a classic Birch reduction in the first step, wherein the compound is reacted in liquid ammonia at −73° C. On a large scale, the use of such low temperatures, and the requirement for large quantities of liquid ammonia are not desirable. The second step is a condensation/annulation reaction in which tin chloride ($SnCl_4$) is used as a Lewis acid catalyst. Because tin is toxic, its use in the reaction so close to the end product is problematic; any trace amounts of tin which may remain in the final product are not desirable for the purpose of human consumption and regulatory approval.

It is, therefore, desirable to provide an improved synthesis of hexahydrodibenzo[b,d]pyran-9-ones that avoids these problems.

SUMMARY OF THE INVENTION

It is an object of the present invention to provide an improved synthesis of hexahydrodibenzo[b,d]pyran-9-ones, which is suited for large scale commercial production.

In a first aspect, the present invention provides a process for preparing a 6a,10a-cis-hexahydrodibenzo[b,d]pyran-9-one of the general formula:

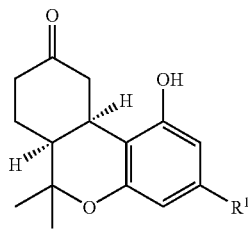

wherein R¹ is $C_{5-10}$-alkyl, $C_{5-10}$-alkenyl, $C_{5-8}$-cycloalkyl, or $C_{5-8}$-cycloalkenyl, and wherein the hydrogen atoms at the 6a and 10a positions are oriented cis to one another, comprising the step of: (ii) reacting a 5-substituted resorcinol of the formula:

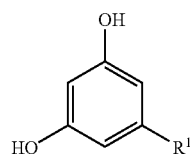

wherein R¹ has the same meaning as above, with a 1-alkoxy-4-(1-hydroxy-1-methylethyl)-1,4-cyclohexadiene of the formula:

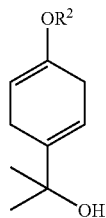

wherein R² is $C_{1-4}$-alkyl, in the presence of a Lewis acid consisting of trifluoromethanesulfonic anhydride (Tf₂O), trifluoromethanesulfonic acid (TfOH), or sulfuric acid.

Other aspects and features of the present invention will become apparent to those ordinarily skilled in the art upon review of the following description of specific embodiments of the invention in conjunction with the accompanying figures.

DETAILED DESCRIPTION

The present invention provides an improved synthesis of 6a,10a-hexahydrodibenzo[b,d]pyran-9-ones, such as nabilone. This invention is especially useful for large scale industrial synthesis, and better complies with cGMP (current Good Manufacturing Practice).

As used herein, the term "6a,10a-cis" refers to the orientation relative to one another of the hydrogen atoms attached at the 6a and 10a positions of the hexahydrodibenzo[b,d]pyran-9-one compounds described herein. Accordingly, compounds which are designated as being "6a,10a-cis" are those compounds wherein the hydrogen atoms attached at the 6a and the 10a positions are oriented on the same side of the plane of the molecule. It will be recognized that at least two isomers are included by the "6a,10a-cis" designation, the 6aR,10aS and the 6aS,10aR isomers. Thus, the designation "6a,10a-cis" includes the separate mirror image isomers of the compounds, known as enantiomers, as well as a mixture of such enantiomers. It will be recognized that at least two isomers are included by the "6a,10a-trans" designation, the 6aS,10aS and the 6aR,10aR isomers. Thus, the designation "6a,10a-trans" includes the separate enantiomers of the compounds, as well as a mixture of such enantiomers.

As used herein, the term "alkyl" means a univalent group derived from an acyclic branched or unbranched saturated hydrocarbon (i.e. containing only carbons and hydrogens) by removal of a hydrogen atom from any carbon atom, and can be represented by $—C_nH_{2n+1}$. The term "$C_{1-4}$-alkyl" is an alkyl group where n is 1-4. Examples of "$C_{1-4}$-alkyl" include methyl, ethyl, n-propyl, isopropyl, n-butyl, and isobutyl. The term "$C_{5-10}$-alkyl" is an alkyl group where n is 5-10. Examples of "$C_{5-10}$-alkyls" include n-pentyl, isohexyl, 1-methylhexyl, 1,2-dimethylheptyl, 1,1-dimethylheptyl, 1,2,3-trimethylheptyl, n-decyl, 1,1-dimethyloctyl, and 1-ethyl-1-methylhexyl.

As used herein, the term "alkenyl" means a univalent group derived from an acyclic branched or unbranched hydrocarbon (i.e. containing only carbons and hydrogens) having one or more carbon-carbon double bonds, where there are a total of at least 2 carbon atoms. When there is only one double bond, the term can be represented by the general formula $—C_nH_{2n-1}$. The term "$C_{5-10}$-alkenyl" is an alkenyl group having 5-10 carbon atoms; thus, where there is only one double bond, i.e. in the formula $—C_nH_{2n-1}$, n is 5-10. Examples of "$C_{5-10}$-alkenyls" include: 2-hexenyl, 3-heptenyl, 1-methyl-1-heptenyl, 1,2-dimethyl-1-heptenyl, 3-octenyl, 1-ethyl-2-octenyl, 1,1-dimethyl-3-octenyl, and related groups.

As used herein, the term "$C_{5-8}$-cycloalkyl" means a univalent group derived from a saturated monocyclic hydrocarbon (with or without side chains) by removal of a hydrogen atom from a ring carbon atom, where the total number of carbon atoms is 5-8. Examples of "$C_{5-8}$-cycloalkyls" include: cyclopentyl, cyclohexyl and cyclooctyl.

As used herein, the term "$C_{5-8}$-cycloalkenyl" means a univalent group derived from a monocyclic hydrocarbon (with or without side chains), having one or more carbon-carbon double bonds in the ring, by removal of a hydrogen atom from a ring carbon atom, where the total number of carbon atoms is 5 to 8. Examples of "$C_{5-8}$-cycloalkenyls" include: 1-cyclohexenyl, 2-cycloheptenyl, 1-cyclooctenyl, and the like.

The process for making 6a,10a-hexahydrodibenzo[b,d]pyran-9-ones by way of the present invention can be represented by the following scheme:

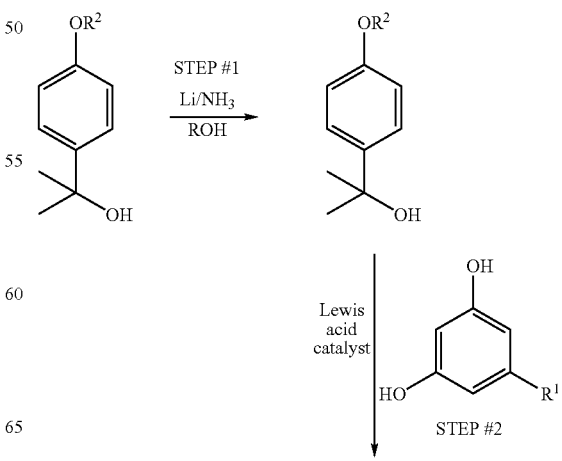

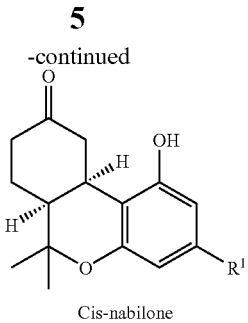

Cis-nabilone

Step #1: Reduction to make a 1-alkoxy-4-(1-hydroxy-1-methyl-ethyl)-1,4-cyclohexadiene: A 2-(4-alkoxy-phenyl)-propan-2-ol is reacted with a Group IA metal in the presence of gaseous ammonia and an alcohol in an organic solvent to form the 1,4-cyclohexadiene derivative. $R^2$ is $C_{1-4}$-alkyl and examples of $C_{1-4}$-alkyl groups include methyl, ethyl, n-propyl, isopropyl, n-butyl, and isobutyl. In one embodiment, $R^2$ is methyl.

The Group IA metal may be lithium, sodium, or potassium. In a particular embodiment, the Group IA metal is lithium. The alcohol is typically ethanol, isopropanol, or t-butanol; in one embodiment the alcohol is t-butanol. This reaction is carried out in an organic solvent, which is not reduced under the conditions of the Birch reduction. Such solvents may include ethers. The solvent may be dioxane or tetrahydrofuran in certain embodiments. In one embodiment, the solvent is tetrahydrofuran (THF).

The reaction is typically carried out at a temperature between −10° C. and 25° C. or between −30° C. to 25° C. However, the reaction may be carried out from −20° C. to 50° C. or from −50° C. to 50° C. In one aspect, the reaction is carried out at room temperature. In another embodiment, the reaction is maintained at a temperature below 0° C. while adding the final reactant and for some time after that (e.g. 1 hour), and then allowed to continue at room temperature.

Generally, the molar ratio of 2-(4-alkoxy-phenyl)-propan-2-ol to lithium to alcohol is 1:4-10:6-10. In one embodiment the ratios are 1:6:6. In another embodiment, the ratios are 1:4:6.

In the initial trials a standard technique was used for work up and isolation of the product. This involved quenching with water or aqueous $NH_4Cl$, separation and evaporation of the upper organic layer followed by partitioning between acetonitrile and hexane. The acetonitrile solution was evaporated to give the target product. However the product was obtained as oil with rather low yields 45-60% and had low purity—80% or less.

A new improved procedure was developed including low temperature crystallization of the cyclohexadiene product from hexane instead of partitioning between acetonitrile and hexane. Moreover, it was found, that the product is easily oxidized on exposure to air producing, therefore all operations were performed under an inert atmosphere. This increased the yield to 75% and the purity of the 1-alkoxy-4-(1-hydroxy-1-methyl-ethyl)-1,4-cyclohexadiene product increased.

Step #2: Annulation to make 6a,10a-cis-hexahydrodibenzo [b,d]pyran-9-one: A 1-alkoxy-4-(1-hydroxy-1-methyl)-ethyl-1,4-cyclohexadiene is reacted with a 5-substituted resorcinol, in the presence of a Lewis acid catalyst and optionally water.

$R^1$ may be a $C_{5-10}$-alkyl group, and includes groups such as n-pentyl, isohexyl, 1-methylhexyl, 1,2-dimethylheptyl, 1,1-dimethylheptyl, 1,2,3-trimethylheptyl, n-decyl, 1,1-dimethyloctyl, and 1-ethyl-1-methylhexyl. Additionally, $R^1$ can be a $C_{5-10}$-alkenyl group, examples of which are 2-hexenyl, 3-heptenyl, 1-methyl-1-heptenyl, 1,2-dimethyl-1-heptenyl, 3-octenyl, 1-ethyl-2-octenyl, 1,1-dimethyl-3-octenyl, and related groups. In addition to alkyl and alkenyl groups, $R^1$ can be either a $C_{5-8}$-cycloalkyl or a $C_{5-8}$-cycloalkenyl moiety. Typical cycloalkyl groups which $R^1$ represents include cyclopentyl, cyclohexyl and cyclooctyl, while cycloalkenyl groups represented by $R^1$ include 1-cyclohexenyl, 2-cycloheptenyl, 1-cyclooctenyl, and the like. In one embodiment, $R^1$ is 1,1-dimethyl-heptyl.

Examples of 5-substituted resorcinols which can be employed in the process of this invention include 5-n-pentyl-resorcinol, 5-n-hexylresorcinol, 5-(1-methyl-2-ethyl-hexyl) resorcinol, 5-(1,1-dimethyl-octyl)resorcinol, 5-(1,2-dimethyl-butyl)resorcinol, 5-(1-hexenyl)resorcinol, 5-(1,2-dimethyl-1-heptenyl)resorcinol, 5-(1-ethyl-2-octenyl) resorcinol, 5-cyclohexylresorcinol, 5-cycloheptylresorcinol, 5-(1-cyclopentenyl)resorcinol, 5-(1-cyclohexenyl)resorcinol, 5-(2-cycloheptenyl)resorcinol, and the like. In one embodiment, the resorcinol is 5-(1,1-dimethyl-heptyl)resorcinol.

In the 1-alkoxy-4-(1-hydroxy-1-methyl-ethyl)-1,4-cyclohexadiene, the $R^2$ is $C_{1-4}$-alkyl and examples of $C_{1-4}$-alkyl groups include methyl, ethyl, n-propyl, isopropyl, n-butyl, and isobutyl. In one embodiment, $R^2$ is methyl. The cyclohexadiene is generally employed in a 0.5-3 molar ratio with respect to the resorcinol. In one embodiment, the cyclohexadiene is employed in a 1.5 molar ratio with respect to the resorcinol.

The choice of catalyst is important, as the yield and the identity of the major product varies dramatically depending on the catalyst. The catalyst may be trifluoromethanesulfonic anhydride ($Tf_2O$) also known as triflic anhydride, trifluoromethanesulfonic acid (TfOH) also known as triflic acid, or sulfuric acid. In one embodiment, the catalyst is triflic anhydride. The catalyst is generally employed in an equimolar quantity or slightly in excess of an equimolar amount with respect to the resorcinol. However, the molar ratio of catalyst to resorcinol can vary from 0.2 to 4; it may be 0.5 to 3.3, it may be 1-2.

Water may be present in the reaction. When using water, the water is generally present in a 0.2 to 4 molar ratio with respect to the resorcinol. In one embodiment, the molar ratio of water to resorcinol is 3-4:1.

The reaction is carried out in an organic solvent, typically a halogenated solvent, ether, or an aromatic solvent. Examples of solvents include dichloromethane (DCM), toluene, THF, hexane, and methyl t-butyl ether (MTBE). Other possible solvents include 1,1-dibromoethane, 1,2-dichloroethane, 1,2-dibromoethane, 1-bromo-2-chloroethane, 1-bromopropane, and chloropropane, benzene, chlorobenzene, xylene, diethyl ether, dimethyl ether, or methyl ethyl ether.

The process can be carried out at any temperature, especially a range from about −30° C. to 30° C., and is conveniently carried out a range from about −20° C. to 20° C. or more particularly at a range from about −20° C. to about 0° C., followed by heating to about room temperature. In one embodiment, the reaction is carried out at a temperature of about −20° C., and then the mixture was allowed to heat to RT.

Conversion to 6a,10a-trans isomer: The 6a,10a-cis isomer may be readily converted to the 6a,10a-trans isomer by methods known in the art, e.g. see column 1 on page 2283 of Archer et al., J. Org. Chem., 42, 2277 (1977).

Synthesis of starting materials: The synthesis of 1-alkoxy-4-(1-hydroxy-1-methyl-ethyl)-benzene is known in the art from a p-alkoxyacetophenone starting material. For example, the p-alkoxyacetophenone can be reacted with methyl magnesium halide, such as methyl magnesium chloride in THF or methyl magnesium bromide in ether ($Et_2O$). See for example column 5 of U.S. Pat. No. 4,148,809 and column 2 on page 2282 of Archer et al., J. Org. Chem., Vol. 42, No. 13, 1977.

The synthesis of resorcinol derivatives is known in the art. See for instance Harrington at al., J. Org. Chem. 2000, Vol. 65, page 6576-6582.

Experimental

Synthesis of
1-methoxy-4-(1-hydroxy-1-methyl-ethyl)-benzene

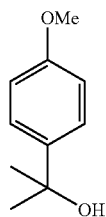

This was synthesized using a synthesis based on that described by Archer et al., J. Org. Chem., Vol. 42, No. 13, 1977, page 2282, column 2 (see synthesis of (22)). A solution of 4-methoxy acetophenone (151.18 g, 1 mol) in 300 ml of anhydrous THF was added for 1 h to the solution of 1N methyl magnesium chloride (1360 ml, 1.36 mol) in THF while maintaining the internal temperature at 10-15° C. After completion of the addition, the reaction mixture was heated for about 4.5 hrs. After completion of the reaction (as determined by TLC), 0.2 L of water was slowly added during 3 hrs to quench the reaction while maintaining the internal temperature at <15° C. The reaction mixture was decanted from the precipitate and evaporated under vacuum. The remaining white residue was washed with methyl t-butyl ether (MTBE) (2×200 mL) and evaporated. The combined residue was dissolved in 400 mL of MTBE and 200 mL of water was added. The organic layer was extracted and the aqueous layer was washed with MTBE (3×50 mL). The combined organic extracts were dried over anhydrous sodium sulfate and evaporated to dryness to afford 156 g of 2-(4-Methoxy-phenyl)-propan-2-ol as yellow oil (94% yield, 96% purity by HPLC).

Synthesis of 1-methoxy-4-(1-hydroxy-1-methyl-ethyl)-1,4-cyclohexadiene (first example of step #1)

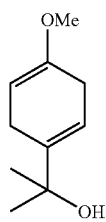

2-(4-methoxy-phenyl)-propan-2-ol (100 g, 0.6 mol) and anhydrous THF (800 ml) were added under argon to a 3 L round bottomed flask equipped with an overhead stirrer, thermometer, dropping funnel, and cooling finger. Granulated lithium (25.1 g, 3.61 mol) was suspended in the solution. The suspension was cooled down to −10° C. and gaseous ammonia was bubbled in until an orange amalgam-like fluid completely covered the suspended metallic lithium. A solution of t-BuOH (345 ml, 3.61 mol) in THF (345 ml) was added while maintaining the temperature below +10° C. The mixture was stirred overnight at room temperature. The reaction was quenched by the slow addition of water (250 ml) keeping the internal temperature below +15° C. Additional water (500 ml) was added to the mixture. The upper organic layer was separated and concentrated by evaporation under vacuum. The residue was dissolved in dichloromethane (DCM) (300 ml), washed with water (2×300 ml), brine (100 ml), and dried over sodium sulfate. The solvent was evaporated under vacuum. The oily residue was partitioned between acetonitrile and hexane. The acetonitrile layer was separated and evaporated to give 58.4 g (58%) of the diene product as a yellowish oil.

Synthesis of 1-methoxy-4-(1-hydroxy-1-methyl-ethyl)-1,4-cyclohexadiene (second example of step #1)

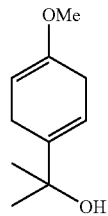

2-(4-methoxy-phenyl)-propan-2-ol (750 g, 4.5 mol), anhydrous THF (7.5 L) and tert-BuOH (2001.4 g, 27 mol) were added under argon to a 22 L round bottomed flask equipped with an overhead stirrer, thermometer and dropping funnel. The mixture was cooled to −30° C. Gaseous ammonia was bubbled through the reaction mixture for 30 min. Granulated lithium (125 g, 18 mol) was added portion wise to the solution during 1-1.5 hr. The stirring was continued with slow flow of ammonia for 20 rh. The reaction was quenched with a solution of 961 g $NH_4Cl$ in 2.7 L water at −20° C. The top layer was separated and evaporated on a rotary evaporator at a bath temperature of 30° C. (all these and subsequent operations are performed under inert atmosphere). The aqueous layer was extracted with MTBE (3×1 L). The concentrate and extract were combined, washed with water and brine, dried over $Na_2SO_4$ and evaporated to dryness at a bath temperature of 35° C. The crude oily product was mixed with 725 ml Hexane and filtered. The filtrate was placed in a freezer at −70° C. and left for 24 hr. The solid was decanted and rinsed with Hexane pre-cooled to −70° C. (2×100 mL) with decantation after each rinsing. After drying under vacuum at 20° C., 562 g of the target product was obtained (yield 74%), having an HPLC purity of 89%.

Synthesis of cis-nabilone (example of step #2)

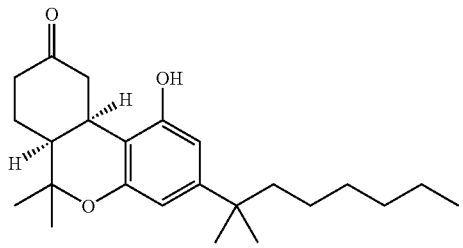

5-(1,1-dimethylheptyl)resorcinol (220 g, 931 mmol) was placed in a 4 neck 3 L round-bottomed flask equipped with an overhead stirrer, thermometer, reflux condenser, and dropping funnel. DCM (1320 ml) was added with stirring. Water (50 ml, 2793 mmol) was added to the stirred suspension, followed by the drop-wise addition of triflic anhydride (263 g, 931 mmol) while maintaining a slow reflux of the solvent until the resorcinol was dissolved. The mixture was cooled to −20° C. and a solution of 1-methoxy-4-(1-hydroxy-1-methyl)-ethyl-1,4-cyclohexadiene (261 g, 1396 mmol) in DCM (250 ml) was added drop-wise, keeping the temperature at −20±3° C. After all the diene was added, the mixture was allowed to warm up to 0° C. and stirred for 2 hours at this temperature. Additional DCM (1000 ml) was added to the reaction mixture and the solution was washed consecutively with water (2×1 L), brine (0.5 L) and dried over sodium sulfate (300 g). The solvent was removed under vacuum. The solidified residue was co-evaporated with hexane (250 ml) to dryness and triturated with a fresh portion of hexane (500 ml) at 65° C. (bath temperature) for 30 min. The suspension was cooled to at 0° C. and kept for 1 h. The precipitate was filtered off, washed with 100 ml of cold hexane and dried under vacuum to a constant weight. Yield 289 g (83.3%) of cis-nabilone.

Using a similar procedure cis-nabilone was also synthesized under the following conditions:

| Solvent | Acid | | Mol. ratio H$_2$O/Resorcinol | Yield % |
| | Name | Mol. ratio acid/Resorcinol | | |
|---|---|---|---|---|
| DCM | Tf$_2$O | 0.5 | 1 | 64 |
| DCM | Tf$_2$O | 1 | 1 | 72 |
| DCM | Tf$_2$O | 1 | 3 | 87 |
| Toluene | Tf$_2$O | 1 | 3 | 81 |
| DCM | TfOH | 1 | 0 | 48 |
| DCM | TfOH | 1 | 0.5 | 60 |
| DCM | TfOH | 1 | 1 | 65 |
| DCM | TfOH | 2 | 0 | 39 |
| Toluene | TfOH | 2 | 3 | 65 |
| DCM | H$_2$SO$_4$ | 0.5 | 0 | 34 |
| DCM | H$_2$SO$_4$ | 3.3 | 0 | 29 |

Conversion of Cis-Nabilone to Trans-Nabilone

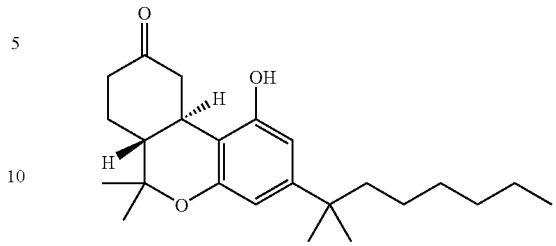

Trans-nabilone was synthesized using the synthesis described by Archer et al., J. Org. Chem., Vol. 42, No. 13, 1977, page 2283, column 1 (see Isomerization of 7 to 6).

The above-described embodiments of the present invention are intended to be non-limiting examples only. Alterations, modifications and variations may be effected to the particular embodiments by those of skill in the art without departing from the scope of the invention, which is defined solely by the claims appended hereto.

All documents mentioned above are incorporated by reference herein.

What is claimed is:

1. A process for preparing a 6a,10a-cis-hexahydrodibenzo[b,d]pyran-9-one of the general formula:

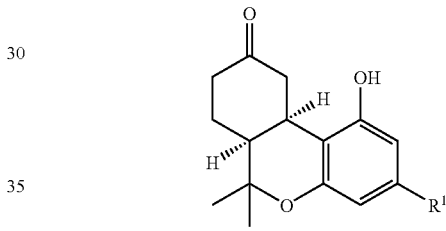

wherein R$^1$ is C$_{5-10}$-alkyl, C$_{5-10}$-alkenyl, C$_{5-8}$-cycloalkyl, or C$_{5-8}$-cycloalkenyl, and wherein the hydrogen atoms at the 6a and 10a positions are oriented cis to one another, comprising the step of:

(ii) reacting a 5-substituted resorcinol of the formula:

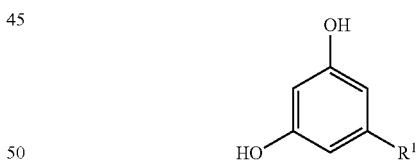

wherein R$^1$ has the same meaning as above, with a 1-alkoxy-4-(1-hydroxy-1-methylethyl)-1,4-cyclohexadiene of the formula:

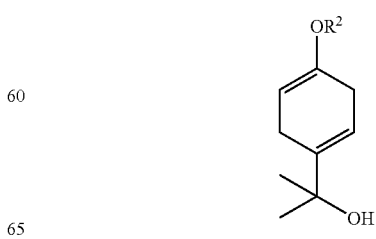

wherein R$^2$ is C$_{1-4}$-alkyl, in the presence of (a) a Lewis acid said Lewis acid being trifluoromethanesulfonic anhydride (Tf$_2$O), trifluoromethanesulfonic acid (TfOH), or sulfuric acid, and (b) an organic solvent.

2. The process of claim 1, wherein the Lewis acid is Tf$_2$O.

3. The process of claim 1, wherein step (ii) is carried out in the presence of water.

4. The process of claim 1, wherein R$^2$ is methyl and R$^1$ is 1,1-dimethyl-heptyl.

5. The process of claim 1, further comprising the step of:
(i) reducing a 1-alkoxy-4-(1-hydroxy-1-methyl-ethyl)-benzene of the formula:

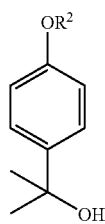

wherein R$^2$ has the same meaning as in claim 1,
in the presence of
(a) an alcohol of formula ROH where R is C$_{1-4}$-alkyl,
(b) gaseous ammonia, and
(c) lithium, sodium, or potassium,
to form the 1-alkoxy-4-(1-hydroxy-1-methyl-ethyl)-1,4-cyclohexadiene of formula

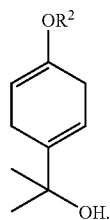

6. The process of claim 5, wherein step (i) is carried out at a temperature range of between −20 and 50° C.

7. The process of claim 6, wherein step (i) is carried out at room temperature, after addition of the alcohol.

8. The process of claim 5, wherein step (i) is carried out in an organic solvent.

9. The process of claim 8, wherein the organic solvent is dioxane or tetrahydrofuran.

10. The process of claim 5, wherein all the process operations are done in inert an atmosphere.

11. The process of claim 10, wherein purification of the 1-alkoxy-4-(1-hydroxy-1-methyl-ethyl)-1,4-cyclohexadiene is performed by crystallization from hexane at a temperature of −60 to −75° C.

12. A process for making a 6a,10a-trans-hexahydrodibenzo[b,d]pyran-9-one, comprising carrying out the process of claim 1, and further comprising the step of:
(iii) reacting the product of step (ii) with AlCl$_3$ to form the 6a,10a-trans product.

* * * * *